United States Patent [19]

Arhancet

[11] Patent Number: 5,538,622
[45] Date of Patent: Jul. 23, 1996

[54] METHODS AND COMPOSITIONS FOR INHIBITING THE POLYMERIZATION OF DICHLOROBUTENE

[75] Inventor: Graciela B. Arhancet, Katy, Tex.

[73] Assignee: Betz Laboratories, Inc., Trevose, Pa.

[21] Appl. No.: 373,707

[22] Filed: Jan. 17, 1995

[51] Int. Cl.$^6$ .................................................. C07C 7/20
[52] U.S. Cl. ............................................ 208/48 AA; 585/5
[58] Field of Search .......................... 585/5; 208/48 AA

[56] References Cited

U.S. PATENT DOCUMENTS 3,878,181  4/1975  Mayer-Mader et al. .............. 260/92.3
4,749,468  6/1988  Roling et al. ...................... 208/48 AA

OTHER PUBLICATIONS

Chemical Abstracts 105(2)): 173217r.
Research Disclosure, 317, 722, Sep. 1990, No. 31734.

*Primary Examiner*—Asok Pal
*Assistant Examiner*—Bekir L. Yildirim
*Attorney, Agent, or Firm*—Alexander D. Ricci; Philip H. Von Neida

[57] ABSTRACT

Methods and compositions for inhibiting the polymerization of crude dichlorobutene during its processing are disclosed. The methods comprise adding an effective polymerization inhibiting amount of a composition of a hydroxylamine compound and a metal deactivator compound to the dichlorobutene. The preferred hydroxylamine compound is bis-(2-hydroxypropyl)hydroxylamine and the preferred metal deactivator compound is a Mannich reaction product.

25 Claims, No Drawings

METHODS AND COMPOSITIONS FOR INHIBITING THE POLYMERIZATION OF DICHLOROBUTENE

FIELD OF THE INVENTION

The present invention relates to methods and compositions for inhibiting the polymerization of crude dichlorobutene during its purification at high temperatures.

BACKGROUND OF THE INVENTION

Dichlorobutenes (3,4-dichlorobutene and 1,4-dichloro-2-butene) are intermediates in the industrial synthesis of chloroprene (2-chloro-1,3-butadiene). Chloroprene gives high molecular weight elastomer polymers or synthetic neoprene used in tires and tire products, rubber goods, footwear, adhesives, latex foams, and latex paints. Most chloroprene is polymerized to make polychloroprene, a synthetic rubber used in wire and cable covers, gaskets, automotive parts, adhesives, and other applications requiring chemical, oil, and weather resistance or high gum strength.

Chloroprene is produced from butadiene in three essential steps. First is chlorination to yield a mixture of dichlorobutene isomers, then isomerization of 1,4-dichloro-2-butene to the desired 3,4-isomer, and, lastly, caustic dehydrochlorination.

Commercial production of chlorobutenes from butadiene is based almost entirely on vapor phase chlorination. The crude chlorination products are condensed from excess butadiene which is then recycled to the reactor. Systems for refining the crude product vary depending on the degree of integration with the subsequent steps, and whether the 1,4-isomer is desired for separate uses or for complete isomerization to the 3,4-isomer. The streams to be separated are (1) low boiling impurities, mainly 1- and 2-chlorobutadiene, (2) purified 3,4-dichlorobutene, (3) 1,4-dichloro-2-butene and (4) high boiling tri- and tetrachlorides. During this purification process, the feedstock must be heated at temperatures from 120° to 160° C. which results in high polymerization and fouling of the purification equipment.

Due to the chlorine content and temperatures employed in the processing system, corrosion of the processing system can occur. This corrosion will cause iron and other metal particles to be present in the dichlorobutene feedstock in amounts as high as 10 parts per million. Iron is a transition metal and its presence in the dichlorobutene feedstock can contribute to the unwanted polymerization of the dichlorobutene.

SUMMARY OF THE INVENTION

The present invention provides for methods for inhibiting the polymerization of dichlorobutene (DCB) during its purification at temperatures of 120° to 160° C. The methods comprise adding a composition of a hydroxylamine compound and a metal deactivator compound to the dichlorobutene during its processing.

DESCRIPTION OF THE RELATED ART

CA 105(20): 173217 r discloses the use of diethylhydroxylamine to inhibit polymerization and fouling in dienes (e.g., butadiene) during purification.

U.S. Pat. No. 3,878,181 discloses methods for terminating the polymerization of chloroprene and/or 2,3-dichlorobutadiene by adding diethylhydroxylamine to the polymerization mixture. Research Disclosure, 317,722, September 1990 in No. 31734 teaches methods for inhibiting the polymerization of 2,3-dichloro-1,3-butadiene in the vapor space above the liquid during shipment. The polymerization is inhibited by adding p-t-butyl catechol (TBC), phenothiazine (PTZ) or an ammonium salt of N-nitrosophenylhydroxylamine (NBH) to the butadiene.

DETAILED DESCRIPTION OF THE INVENTION

The present invention provides for methods and compositions for inhibiting the polymerization of dichlorobutene during processing comprising adding to said dichlorobutene an effective polymerization inhibiting amount of a combination of a hydroxylamine compound and a metal deactivator compound.

The methods of the present invention are effective at inhibiting the polymerization of dichlorobutene (DCB) under processing conditions. These processing conditions include but are not limited to the purification and distillation processes of dichlorobutene which occur at temperatures from 120° to 160° C.

The hydroxylamine compounds useful in this invention generally have the formula:

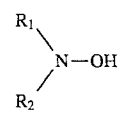

wherein $R_1$ and $R_2$ are the same or different and are hydrogen, alkyl, aryl, alkaryl, aralkyl, or hydroxyalkyl groups and preferably have three to about twenty carbon atoms. The preferred hydroxylamine compounds are hydroxyalkylhydroxylamine (HAHA) compounds and the most preferred compound is bis-(2-hydroxypropyl)hydroxylamine (HPHA).

The preferred metal deactivator compound for use in the present invention is a Mannich reaction product.

The Mannich reaction product is formed by reaction of reactants (A), (B) and (C); wherein (A) is an alkyl substituted phenol of the structure:

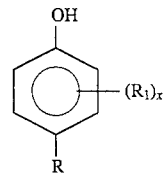

wherein R and $R_1$ are the same or different and are independently selected from alkyl, aryl, alkaryl, or aralkyl of from 1 to about 20 carbon atoms, x is 0 or 1; wherein (B) is a polyamine of the structure:

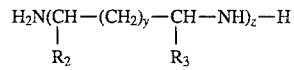

wherein z is a positive integer, $R_2$ and $R_3$ may be the same or different and are independently selected from H, alkyl, aryl, aralkyl, or alkaryl having from 1 to about 20 carbon atoms, y is 0 or 1; and wherein (C) is an aldehyde of the structure:

wherein $R_4$ is selected from H and an alkyl having from 1 to about 6 carbon atoms.

The alkyl substituted phenol may be selected from the group including but not limited to p-cresol, 4-ethylphenol, 4-t-butylphenol, 4-t-amylphenol, 4-t-octylphenol, 4-dodecylphenol, 2,4-di-t-butylphenol, 2,4-di-t-amylphenol, and 4-nonylphenol. The preferred alkyl substituted phenol is 4-nonylphenol.

The polyamine may be selected from the group including but not limited to ethylenediamine, propylene diamine, diethylene triamine, triethylene tetramine, tetraethylene pentamine with ethylenediamine being preferred.

The aldehyde may be selected from the group including but not limited to formaldehyde, acetaldehyde, propanaldehyde, butyraldehyde, hexaldehyde and heptaldehyde. The preferred aldehyde is formaldehyde in its monomeric form or, more conveniently, in its polymeric form (i.e., paraformaldehyde).

As is conventional in the art, the condensation reaction may proceed at temperatures from about 50° to 200° C. with a preferred temperature range being about 75° to 175° C. As is stated in U.S. Pat. No. 4,166,726, the time required for completion of the reaction usually varies from about 1 to 8 hours, varying of course with the specific reactants chosen and the reaction temperature.

The molar range of the components (A):(B):(C) which may be used is in the range 0.5–5:1:0.5–5. A preferred embodiment (A):(B):(C) is p-nonylphenol: ethylenediamine: paraformaldehyde in a 2:1:2 molar ratio of components. Various examples of this Mannich reaction product are described in U.S. Pat. No. 4,749,468, the contents of which are wholly incorporated by disclosure herein.

The total amount of the composition of hydroxylamine compound and metal deactivator compound used in the methods of the present invention is that amount which is sufficient to inhibit polymerization and will vary according to the conditions and temperatures under which the dichlorobutene is being processed. At higher temperature conditions and higher contamination of the crude dichlorobutene, larger amounts of this composition are generally required.

Preferably, the total amount of the composition added to the dichlorobutene ranges from 1 part to about 1000 parts per million parts dichlorobutene. More preferably, the treatment range is from about 10 parts of the composition to about 250 parts per million parts of the dichlorobutene.

The weight ratio of hydroxylamine compound to metal deactivator compound ranges from about 9:1 to about 1:9 with a ratio of 2:1 preferred.

The compositions of the present invention can be added to the dichlorobutene by any conventional method, either as individual ingredients or as a combination of ingredients. It is preferred to add the composition as a single treatment.

The composition of the present invention may be added to the dichlorobutene as either a dispersion or as a solution using a suitable liquid carrier or solvent. Any solvent that is compatible with the individual components of the composition and the dichlorobutene may be employed. Preferred solvents include but are not limited to aromatic naphtha.

Accordingly, it is possible therefore to produce a more effective dichlorobutene polymerization treatment than is obtainable by the use of either ingredient alone when measured at comparable treatment levels. This enhanced activity allows for the concentration of each of the ingredients to be lowered and the total quantity of polymerization inhibitor required, particularly at higher processing temperatures, may be reduced.

The preferred inventive embodiment employs bis-(2-hydroxypropyl)hydroxylamine and Mannich reaction product in a weight ratio of 2 to 1.

The invention will now be further described with reference to a number of specific examples which are to be registered solely as illustrative, and not as restricting the scope of the invention.

EXAMPLES

The polymerization inhibiting activity of hydroxylamine compounds and metal deactivators in dichlorobutene was evaluated. Crude dichlorobutene (50 mL), with the appropriate treatment, was placed in a glass flask contained in a stainless steel vessel, pressurized with nitrogen (200 psi), and immersed in an oil bath heated at 250° F. Heating continued for two hours. At the end of this time the mixture was transferred to a preweighed beaker and the liquid was evaporated on a heating block until the polymer residue was obtained. The beakers were weighed again and the amount of polymer was recorded. This is compared to the initial polymer present in the crude dichlorobutene which is determined by evaporation of 50 mL of feedstock as described above. Results of this testing are presented in Table I.

TABLE I

| Treatment | Heat induced gum testing 250° F. for 2 hours | | |
|---|---|---|---|
| | Dose (ppm) | Total Gum (mg/50 mL) | Net Gum* (mg/50 mL) |
| Run 1 | | | |
| Blank | — | 85 | 56 |
| PTZ | 40 | 51 | 22 |
| HPHA | 50 | 52 | 23 |
| Run 2 | | | |
| Blank | — | 61 | 21 |
| HPHA/MD | 40:4 | 41 | 1 |
| HPHA/MD | 25:10 | 44 | 4 |

*Net gum = total gum − initial gum
PTZ is phenothiazine
HPHA is bis-(2-hydroxypropyl)hydroxylamine
MD is the Mannich reaction product as described in U.S. Pat. No. 4,749,468 of p-nonylphenol, ethylenediamine and paraformaldehyde in a molar ratio of 2:1:2.

The testing results of Run 2 indicate the good polymerization inhibition demonstrated by the hydroxylamine compound and Mannich reaction product of the present invention. These results further demonstrate that combinations of a hydroxylamine compound and a metal deactivator in ratios of 2.5:1 to 10:1 are effective at inhibiting the polymerization of crude dichlorobutene. Further, these results demonstrate that the combination is more effective than a known inhibitor, phenothiazine, or HPHA when used by itself.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

Having thus described the invention, what I claim is:

1. A method for inhibiting the polymerization of dichlorobutene during dichlorobutene processing comprising adding to said dichlorobutene an effective polymerization inhibiting amount of a combination of a hydroxylamine compound and a Mannich reaction product.

2. The method as claimed in claim 1 wherein said hydroxylamine compound has the formula:

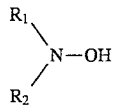

wherein $R_1$ and $R_2$ are the same or different and are hydrogen, alkyl, aryl, alkaryl, aralkyl, or hydroxyalkyl groups and preferably have three to about twenty carbon atoms.

3. The method as claimed in claim 2 wherein said hydroxylamine compound is a hydroxyalkylhydroxylamine compound.

4. The method as claimed in claim 3 wherein said hydroxylamine is bis-(2-hydroxypropyl)hydroxylamine.

5. The method as claimed in claim 1 wherein said Mannich reaction product is a Mannich reaction product formed by reaction of reactants (A), (B), and (C), wherein (A) comprises an alkyl substituted phenol of the structure:

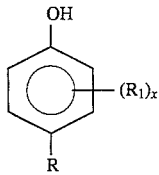

wherein R and $R_1$ are the same or different and are independently selected from alkyl, aryl, alkaryl, or aralkyl of from 1 to about 20 carbon atoms, x is 0 or 1; (B) comprises a polyamine of the structure:

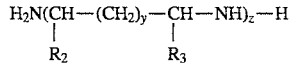

wherein z is a positive integer, $R_2$ and $R_3$ may be the same or different and are independently selected from H, alkyl, an/l, aralkyl, or alkaryl having from 1 to about 20 carbon atoms, y is 0 or 1; and (C) is an aldehyde of the structure:

wherein $R_4$ comprises H or $C_1$ to $C_6$ alkyl.

6. The method as claimed in claim 5 wherein the molar ratio of reactants (A):(B):(C) is 0.5 to 5:1:0.5 to 5.

7. The method as claimed in claim 5 wherein (A) is selected from the group consisting of p-cresol, 4-ethylphenol, 4-t-butylphenol, 4-t-amylphenol, 4-t-octylphenol, 4-dodecylphenol, 2,4-di-t-butylphenol, 2,4-di-t-amylphenol, and 4-nonylphenol.

8. The method as claimed in claim 5 wherein (B) is selected from the group consisting of ethylenediamine and triethylenetetramine.

9. The method as claimed in claim 5 wherein (C) is selected from the group consisting of formaldehyde and paraformaldehyde.

10. The method as claimed in claim 1 wherein the weight ratio of hydroxylamine compound to Mannich reaction product ranges from 9:1 to 1:9.

11. The method as claimed in claim 1 wherein said dichlorobutene processing is selected from the group consisting of purification and distillation.

12. The method as claimed in claim 1 wherein said dichlorobutene is at a temperature from about 120° to about 160° C.

13. The method as claimed in claim 1 wherein said combination is added to said dichlorobutene in an amount ranging from 1 part to about 1000 parts per million parts of said dichlorobutene.

14. The method as claimed in claim 1 wherein said combination is added to said dichlorobutene in a liquid carrier solvent.

15. The method as claimed in claim 14 wherein said liquid carrier solvent is aromatic naphtha.

16. A composition having utility at inhibiting the polymerization of dichlorobutene comprising a hydroxylamine compound and a Mannich reaction product formed by reaction of reactants (A), (B), and (C), wherein (A) comprises an alkyl substituted phenol of the structure:

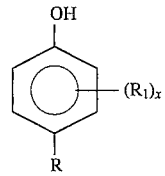

wherein R and $R_1$ are the same or different and are independently selected from alkyl, aryl, alkaryl, or aralkyl of from 1 to about 20 carbon atoms, x is 0 or 1; (B) comprises a polyamine of the structure:

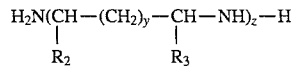

wherein z is a positive integer, $R_2$ and $R_3$ may be the same or different and are independently selected from H, alkyl, aryl, aralkyl, or alkaryl having from 1 to about 20 carbon atoms, y is 0 or 1; and (C) is an aldehyde of the structure:

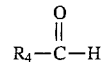

wherein $R_4$ comprises H or $C_1$ to $C_6$ alkyl.

17. The composition and claimed in claim 16 wherein said hydroxylamine compound has the formula:

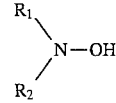

wherein $R_1$ and $R_2$ are the same or different and are hydrogen, alkyl, aryl, alkaryl, aralkyl, or hydroxyalkyl groups and preferably have three to about twenty carbon atoms.

18. The composition as claimed in claim 17 wherein said hydroxylamine compound is a hydroxyalkylhydroxylamine compound.

19. The composition as claimed in claim 18 wherein said hydroxyalkylhydroxylamine compound is bis-(2-hydroxypropyl) hydroxylamine.

20. The composition as claimed in claim 16 wherein the molar ratio of reactants (A):(B):(C) in said Mannich reaction product is 0.5 to 5:1:0.5 to 5.

21. The composition as claimed in claim 20 wherein (A) is selected from the group consisting of p-cresol, 4-ethylphenol, 4-t-butylphenol, 4-t-amylphenol, 4-t-octylphenol, 4-dodecylphenol, 2,4-di-t-butylphenol, 2,4-di-t-amylphenol, and 4-nonylphenol. The preferred alkyl substituted phenol is 4-nonylphenol.

22. The composition as claimed in claim 20 wherein (B) is selected from the group consisting of ethylenediamine and triethylenetetramine.

23. The composition as claimed in claim 20 wherein (C) is selected from the group consisting of formaldehyde and paraformaldehyde.

24. The composition as claimed in claim 16 wherein the weight ratio of hydroxylamine compound to Mannich reaction product ranges from 9:1 to 1:9.

25. The composition as claimed in claim 16 further comprising dichlorobutene.

\* \* \* \* \*